United States Patent [19]

Levin

[11] Patent Number: 5,352,820

[45] Date of Patent: Oct. 4, 1994

[54] EXPEDIENT ROUTE TO ARYL PROPENOIC ESTERS

[76] Inventor: Jeremy I. Levin, 190 Treetop Cir., Nanuet, N.Y. 10954

[21] Appl. No.: 83,817

[22] Filed: Jun. 28, 1993

[51] Int. Cl.$^5$ .............................................. C07C 69/76
[52] U.S. Cl. ..................................... 560/104; 560/21; 560/51; 560/56; 560/81; 560/100; 548/562; 549/79; 549/505; 549/506
[58] Field of Search ................... 560/104, 100, 21, 51, 560/56, 81; 548/562; 549/79, 505, 506

[56] References Cited

U.S. PATENT DOCUMENTS

| | | | |
|---|---|---|---|
| 4,309,350 | 1/1982 | Holan et al. | 560/104 |
| 4,554,360 | 11/1985 | Yamazaki et al. | 560/104 |
| 5,041,618 | 8/1991 | Brand et al. | 560/104 |
| 5,276,217 | 1/1994 | Tius et al. | 560/104 |

FOREIGN PATENT DOCUMENTS 3821503 12/1989 Fed. Rep. of Germany .

OTHER PUBLICATIONS

John C. Cochran et al., Palladium(0) Catalysis in Hydrostannation of Carbon–Carbon Triple Bonds, Tetrahedron Letters, vol. 31, No. 46, pp. 6621–6624, 1990.

H. X. Zhang et al., Palladium and Molybdenum–Catalyzed Hydrostannation of Alkynes, J. Org. Chem., 1990, 55, 1857–1867.

*Primary Examiner*—Paul J. Killos

[57] ABSTRACT

The invention is an expedient route to synthesizing substituted or unsubstituted aryl-2-propenoic esters. The substituted or unsubstituted aryl-2-propenoic esters are useful in preparing optically active substituted or unsubstituted 2-arylpropanoic acids known to be active anti-inflammatory agents.

40 Claims, No Drawings

EXPEDIENT ROUTE TO ARYL PROPENOIC ESTERS

FIELD OF THE INVENTION

The invention is an expedient route to synthesizing substituted or unsubstituted aryl-2-propenoic esters. The substituted or unsubstituted aryl-2-propenoic esters are useful in preparing optically active substituted or unsubstituted 2-arylpropanoic acids known to be active anti-inflammatory agents.

SUMMARY OF THE INVENTION

The invention is a process for making a substituted or unsubstituted aryl-2-propenoic ester of formula I:

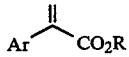

wherein
Ar is

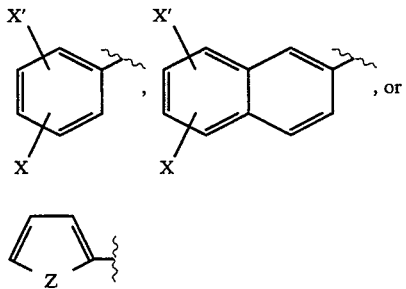

Z is NH, O or S;
X and X' are independently hydrogen, ($C_1$-$C_4$)alkyl, ($C_1$-$C_4$)alkoxy, ($C_1$-$C_4$)alkanoyl, ($C_1$-$C_4$)alkoxycarbonyl, trifluoromethyl, nitro, bromine, chlorine, fluorine, phenyl, substituted phenyl [wherein the substitution is hydrogen, ($C_1$-$C_4$)alkyl, ($C_1$-$C_4$)alkoxy, ($C_1$-$C_4$)alkanoyl, ($C_1$-$C_4$)alkoxycarbonyl, trifluoromethyl, nitro, bromine, chlorine or fluorine], thiophene, pyridine or furan; and R is ($C_1$-$C_4$)alkyl;
which comprises:
reacting a substituted or unsubstituted aryl iodide of the formula:

Ar—I            1 wherein Ar is as defined hereinabove;
with an α-stannyl acrylate ester of the formula:

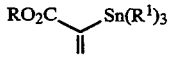            3 wherein R is as defined hereinabove and $R^1$ is ($C_1$-$C_4$)alkyl;
in the presence of palladium(O) or palladium(II), and copper(I or II) catalyst, in a polar-aprotic solvent at room temperature for from 1 to 100 hours and recovering the substituted or unsubstituted aryl-2-propenoic ester so produced. The substituted or unsubstituted aryl-3-propenoic ester is not produced.

Alternatively, substituted or unsubstituted aryl-2-propenoic esters of formula I, wherein Ar is as defined hereinabove, can be made by reacting a substituted or unsubstituted aryl triflate of the formula:

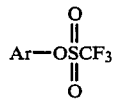            2 wherein Ar is as defined hereinabove;
with an α-stannyl acrylate ester of the formula:

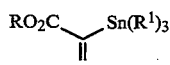            3 wherein R and $R^1$ are as defined hereinabove; in the presence of palladium(0) or palladium(II), copper(I or II), and lithium chloride catalyst, in a polar-aprotic solvent at room temperature for from 1 to 100 hours and recovering the substituted or unsubstituted aryl-2-propenoic ester so produced. The substituted or unsubstituted aryl-3-propenoic ester is not produced.

The above conditions have not been used previously to couple vinyl stannanes with aryl triflates.

The palladium catalyzed coupling of a vinyl stannane 3, wherein R is ethyl and $R^1$ is n-butyl, with a uridine triflate provides a 1:1 mixture of the acrylate and cinnamate esters [B. Flynn, V. Macolino, G. T. Crisp, Nucleosides & Nucleotides, 10, 763 (1991)].

The palladium catalyst is bis(triphenylphosphine)palladium(II) chloride, bis(benzonitrile)palladium(II) chloride, trans-benzyl(chloro)bis(triphenylphosphine)palladium(II) or tetrakis(triphenylphosphine)palladium(0).

The copper catalyst is copper(I) iodide, copper(I) bromide, copper(I) cyanide, copper(I) bromidedimethyl sulfide complex or copper(II) bromide.

DETAILED DESCRIPTION OF THE INVENTION

The process and compounds of the present invention are described in the following reaction:

SCHEME 1

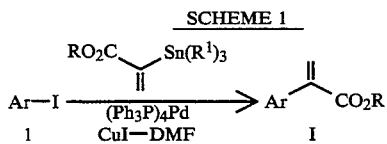

In accordance with Scheme 1, 1 mmol of substituted or unsubstituted aryl iodide 1, wherein Ar, Z, X and X' are as defined hereinabove, dissolved in a polar-aprotic solvent, is reacted with 2.5 mmol of 2-(tributylstannyl)-2-propenoic acid methyl ester [made by the procedure of J. C. Cochran, et. al., Tet. Lett. 31 (46) 6621(1990) or F. Guibe, et. al., J. Org. Chem. 55,1857(1990)], 0.10 mmol tetrakis(triphenylphosphine)palladium(0), and 0.75 mmol copper(1) iodide for from 1–100 hours at room temperature. The reaction solution is diluted with diethyl ether, filtered through diatomaceous earth, washed, dried and concentrated In vacuo. The residue is purified by flash chromatography (silica gel: ethyl acetate/hexane) to give the desired substituted or unsubstituted aryl-2-propenoic ester in excellent yield.

SCHEME 1

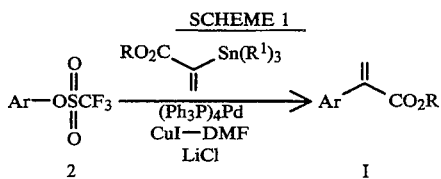

Alternatively, in accordance with Scheme 2, 1 mmol of substituted or unsubstituted aryl triflate, 2, wherein Ar, Z, X and X,are as defined hereinabove, dissolved in a polar-aprotic solvent, is reacted with 2.5 mmol of 2-(tributylstannyl)-2-propenoic acid methyl ester made by the procedure of J. C. Cochran, et. al., *Tet. Lett.* 31 (46) 6621(1990) or F. Guibe, et. al., *J. Org. Chem.* 55,1857(1990)], 0.10 mmol tetrakis(triphenylphosphine)-palladium(0), 0.75 mmol copper(1) iodide and 3.00 mmol lithium chloride for from 1–100 hours at room temperature. The reaction solution is diluted with diethyl ether, filtered through diatomaceous earth, washed, dried and concentrated in vacuo. The residue is purified by flash chromatography (silica gel: ethyl acetate/hexane) to give solely the desired substituted or unsubstituted aryl-2-propenoic ester in excellent yield.

The following non-limiting examples illustrate the process of the present invention.

General Procedure for Coupling 2-(tributylstannyl-2-propenoic acid methyl ester, 3, to Aryl Iodides 1

To a solution of 1.0 mmol of an aryl iodide or substituted aryl iodide, 1, in 10 ml of dimethylformamide is added 2.50 mmol of 2-(tributylstannyl)-2-propenoic acid methyl ester 3 and 0.10 mmol of tetrakis(triphenylphosphine)palladium(0). To this stirred reaction mixture is then added 0.75 mmol of copper(I) iodide in one portion. After 15 minutes at room temperature, the reaction is homogeneous and the solution developed a dark brown color. The reaction is stirred at room temperature until all the starting iodide is consumed, usually 12–48 hours. The reaction progress is monitored by thin layer chromatography.

The reaction mixture is diluted with 100 ml of diethyl ether and filtered through diatomaceous earth. The filtrate is washed with water, saturated sodium chloride, dried, filtered and concentrated in vacuo. The residue is purified by flash chromatography on silica gel, eluting with ethyl acetate/hexanes to provide the desired product.

Substantially following the method described in detail hereinabove, the compounds of this invention listed below in Examples 1–8 are prepared.

EXAMPLE 1

α-Methylene-4-nitrobenzeneacetic acid methyl ester

Yield=76%.

$^1$H NMR (CDCl$_3$): δ8.22(d,2H, J=8.9 Hz); 7.59(d,2H, J=8.9 Hz); 6.56(s,1H); 6.04(s,1H); 3.86(s,3H).

IR (KBr): 3111, 2960, 1723, 1509, and 1344 cm$^{-1}$.

MS(CI)=m/z 208(MH+).

EXAMPLE 2

α-Methylene-4-(trifluoromethyl)benzeneacetic acid methyl ester

Yield=72%.

$^1$H NMR (CDCl$_3$): δ7.62(d,2H, J=8.3 Hz); 7.52(d,2H, J=8.3 Hz); 6.48(d,1H, J=0.9 Hz); 5.97(d,1H, J=0.9 Hz); 3.84(s,3H).

IR (neat): 2957, 1727, 1616, and 1326 cm$^{-1}$.

MS (CI): m/z 231 (MH+).

EXAMPLE 3

4-Acetyl-α-methylenebenzeneacetic acid methyl ester

Yield=78%.

$^1$H NMR (CDCl$_3$): δ7.95(d,2H, J=8.7 Hz); 7.52(d,2H, J=8.6 Hz); 6.47(d,1H, J=0.9 Hz); 5.98(d,1H, J=0.9 Hz); 3.84(s,3H).

IR (KBr): 2959, 1721, 1679, 1606, 1344, and 1206 cm$^{-1}$.

MS(CI): m/z 205(MH+).

EXAMPLE 4

4-(Methoxycarbonyl)-α-methylenebenzeneacetic acid methyl ester

Yield=66%.

$^1$H NMR (CDCl$_3$): δ8.03(d,2H, J=8.5 Hz); 7.49(d,2H, J=8.5 Hz); 6.46(d,1H, J=0.9 Hz); 5.97(d,1H, J=0.9 Hz); 3.93(s,3H); 3.84(s,3H).

IR (KBr): 1720, 1710, 1606, 1438, and 1282 cm$^{-1}$.

MS(CI): m/z 221(MH+).

EXAMPLE 5

α-Methylenebenzeneacetic acid methyl ester

Yield=87%.

$^1$H NMR (CDCl$_3$): δ7.38(m,5H); 6.35(d,1H, J=0.8 Hz); 5.87(d,1H, J=0.7 Hz); 3.79(s,3H).

IR (neat): 2845, 1723, 1496, and 1203 cm$^{-1}$.

MS(CI): m/z 163(MH+).

EXAMPLE 6

4-Methyl-α-methylenebenzeneacetic acid methyl ester

Yield=71%.

$^1$H NMR (CDCl$_3$): δ7.30(d,2H, J=8.2 Hz); 7.16(d,2H, J=8.0 Hz); 6.31(d,2H, J=1.2 Hz); 5.86(d,2H, J=1.3 Hz); 3.82(s,3H); 2.36(s,3H).

IR (neat): 2953, 1736, 1513, and 1436cm$^{-1}$.

MS(CI): m/z 177(MH+).

EXAMPLE 7

4-Bromo-α-methylenebenzeneacetic acid methyl ester

Yield=92%.

$^1$H NMR (CDCl$_3$): δ7.46(d,2H, J=8.6 Hz); 7.28(d,2H, J=8.5 Hz); 6.38(d,1H, J=0.9 Hz); 5.89(d,1H, J=0.9 Hz); 3.81(s,3H).

IR (neat): 2954, 1725, 1488, and 1457 cm$^{-1}$.

MS(CI): m/z 241 and 243(MH+).

EXAMPLE 8 p-Methoxyatropic acid methyl ester Yield=42%.

$^1$H NMR (CDCl$_3$): δ7.36(d,2H, J=8.8 Hz); 6.88 (d,2H, J=8.8 Hz); 6.27(d,1H, J=1.0 Hz); 5.83(d,2H, J=1.1 Hz); 3.82(s,6H).

IR (neat): 2953, 1723, 1609 and 1513cm$^{-1}$.

MS(CI): m/z 193 (MH+).

EXAMPLE 9

Trifluoromethanesulfonic acid 6-methoxy-2-naphthalenyl ester

To a 0° C. solution of 0.50 g of 6-methoxy-2-naphthol in 1.4 ml of dry pyridine is added 0.49 ml of triflic anhydride. The reaction is allowed to warm to room temperature and stirred for 24 hours. The mixture is poured into a solution of 50 ml of water and 50 ml of diethyl ether. The aqueous layer is extracted three times with diethyl ether and the combined organic layers are dried, filtered and concentrated in vacuo. The residue is purified by chromatography (silica gel: ethyl acetate/hexane) to give 0.67 g (76% yield) of the desired product as a colorless oil.

$^1$H NMR (CDCl$_3$): δ7.75(m,3H), 7.25(m,3H); 3.93(s,3H).

IR (neat) 1633, 1607, 1512, and 1422cm$^{-1}$.

MS(CI): m/z 307(MH+).

EXAMPLE 10

6-Methoxy-α-methylene-2-naphthaleneacetic acid methyl ester

To a room temperature solution of 0.306 g of product from Example 9 in 10 ml of dimethylformamide is added 0.938 g of 2-(tributylstannyl)-2-propenoic acid methyl ester, 0.116 g of tetrakis(triphenylphosphine)-palladium(0), 0.143 g of copper(1)iodide and 0.128 g of lithium chloride. The resulting reaction mixture is stirred, at room temperature, for 48 hours and then poured into 100 ml of diethyl ether. The layers are separate, the organic layer is washed with water and saturated sodium chloride, dried, filtered and concentrated in vacuo. The residue is purified by chromatography (silica gel: ethyl acetate/hexane 1/20) to give 0.171 g (71% yield) of the desired product as a white solid.

$^1$H NMR (CDCl$_3$): δ7.75(m,3H); 7.49(d,1H, J=8.5 Hz); 7.16(m,2H); 6.39(s,10H); 5.99(s,1H); 3.92(s,3H); 3.85(s,3H).

IR (KBr): 3036, 1713, 1605, 1435, 1320, and 1262cm$^{-1}$.

MS(CI): m/z 243(MH+).

I claim:

1. The process for making a substituted or unsubstituted aryl-2-propenoic ester of formula I:

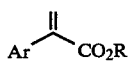

I wherein
Ar is

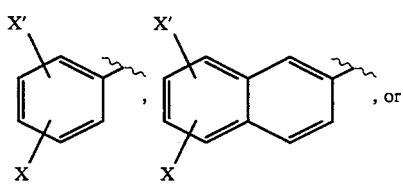, or

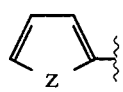

Z is NH, O or S;

X and X' are independently hydrogen, (C$_1$-C$_4$)alkyl, (C$_1$-C$_4$)alkoxy, (C$_1$-C$_4$)alkanoyl, (C$_1$-C$_4$)alkoxycarbonyl, trifluoromethyl, nitro, bromine, chlorine, fluorine, phenyl, substituted phenyl wherein the substitution is hydrogen, (C$_1$-C$_4$)alkyl, (C$_1$-C$_4$)alkoxy, (C$_1$-C$_4$)alkanoyl, (C$_1$-C$_4$)alkoxycarbonyl, trifluoromethyl, nitro, bromine, chlorine or fluorine, thiophene, pyridine or furan; and R is (C$_1$-C$_4$)alkyl;

which comprises:

reacting a substituted or unsubstituted aryl iodide of the formula:

wherein Ar is as defined hereinabove;
with an α-stannyl acrylate ester of the formula:

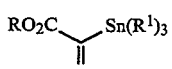     3 wherein R is as defined hereinabove and R$^1$ is (C$_1$-C$_4$)alkyl;

in the presence of palladium(0) or palladium(II), and copper(I or II) catalyst, in a polar-aprotic solvent at room temperature for from 1 to 100 hours and recovering the substituted or unsubstituted aryl-2-propenoic ester so produced.

2. The process for making substituted or unsubstituted aryl-2-propenoic esters of formula I,

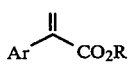

I wherein
Ar is

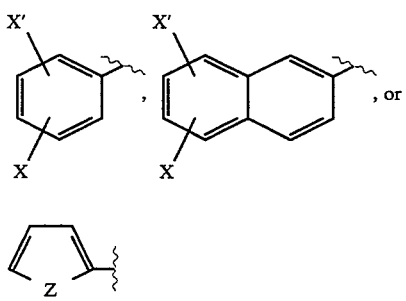, or

Z is NH, O or S;

X and X' are independently hydrogen, (C$_1$-C$_4$)alkyl, (C$_1$-C$_4$)alkoxy, (C$_1$-C$_4$)alkanoyl, (C$_1$-C$_4$)alkoxycarbonyl, trifluoromethyl, nitro, bromine, chlorine, fluorine, phenyl, substituted phenyl wherein the substitution is hydrogen, (C$_1$-C$_4$)alkyl, (C$_1$-C$_4$)alkoxy, (C$_1$-C$_4$)alkanoyl, (C$_1$-C$_4$)alkoxycarbonyl, trifluoromethyl, nitro, bromine, chlorine or fluorine, thiophene, pyridine or furan; and R is (C$_1$-C$_4$)alkyl;

which comprises:

reacting a substituted or unsubstituted aryl triflate of the formula;

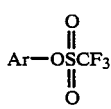

with an α-stannyl acrylate ester of the formula:

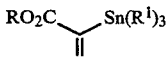

wherein R is as defined hereinabove and $R^1$ is $(C_1-C_4)$alkyl;

in the presence of palladium(0) or palladium(II), copper(I or II), and lithium chloride catalyst, in a polar-aprotic solvent at room temperature for from 1 to 100 hours and recovering substituted or unsubstituted aryl-2-propenoic esters so produced.

3. The process for making compounds according to claim 1, wherein Ar is

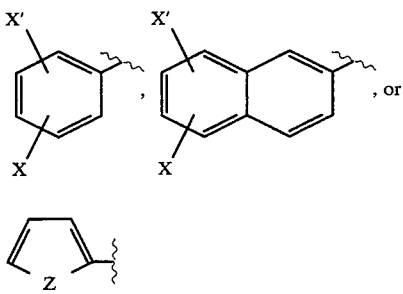

Z is NH, O or S;

X is hydrogen and X' is hydrogen, $(C_1-C_4)$alkyl, $(C_1-C_4)$alkoxy, $(C_1-C_4)$alkanoyl, $(C_1-C_4)$alkoxycarbonyl, trifluoromethyl, nitro, bromine, chlorine or fluorine.

4. The process for making compound according to claim 3, wherein Ar is phenyl, X is hydrogen and X' is hydrogen, methyl, methoxy, acyl, methoxycarbonyl, trifluoromethyl, nitro or bromo.

5. The process for making compounds according to claim 2, wherein Ar is

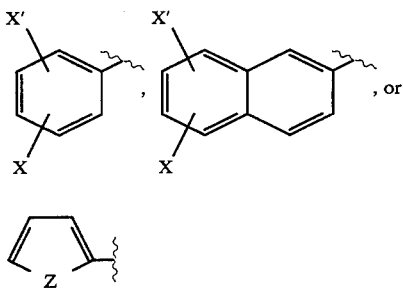

Z is NH, O, or S;

X is hydrogen, and X' is hydrogen, $(C_1-C_4)$alkyl, $(C_1-C_4)$alkoxy, $(C_1-C_4)$alkanoyl, $(C_1-C_4)$alkoxycarbonyl, trifluoromethyl, nitro, bromine, chlorine or fluorine.

6. The process for making compounds according to claim 5, wherein Ar is

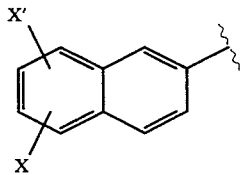

X is hydrogen and X' is hydrogen, methyl, methoxy, acyl, methoxycarbonyl, trifluoromethyl, nitro or bromo.

7. The process of claim 1, wherein the polar-aprotic solvent is dimethylformamide, N-methyl-pyrrolidinone, or dimethylacetamide.

8. The process of claim 7, wherein the polar-aprotic solvent is dimethylformamide.

9. The process of claim 1, wherein the range of molar ratio of substituted or unsubstituted aryl iodide to α-stannyl acrylate ester is 1:0.5 to 1:10.

10. The process of claim 7, wherein the molar ratio of substituted or unsubstituted aryl iodide to α-stannyl acrylate ester is 1:2.5.

11. The process of claim 1, wherein the palladium catalysts are bis(triphenylphosphine)palladium(II) chloride, bis(benzonitrile)palladium(II) chloride, trans-benzyl(chloro)bis(triphenylphosphine)palladium(II) or tetrakis(triphenylphosphine)palladium(0).

12. The process of claim 11, wherein the palladium(0) catalyst is terakis(triphenylphosphine)palladium(0).

13. The process of claim 1, wherein the range of molar ratio of terakis(triphenylphosphine)palladium(0). is 1 to 15% of the substituted or unsubstituted aryl iodide.

14. The process of claim 13, wherein the molar ratio of terakis(triphenylphosphine)palladium(0) is 10% of the substituted or unsubstituted aryl iodide.

15. The process of claim 1, wherein the copper(I or II) catalyst is copper(I) iodide, copper(I) bromide, copper(I) cyanide, copper(I) bromide-dimethyl sulfide complex or copper(II) bromide.

16. The process of claim 15, wherein the copper(I or II) catalyst is copper(I) iodide.

17. The process of claim 1, wherein the range of molar ratio of copper(I) iodide catalyst is 10 to 150% of the substituted or unsubstituted aryl iodide.

18. The process of claim 17 wherein the the molar ratio of copper(I) iodide is 75% of the substituted or unsubstituted aryl iodide.

19. The process of claim 2, wherein the polar-aprotic solvent is dimethylformamide, N-methylpyrrolidinone, or dimethylacetamide, 20. The process of claim 19, wherein the polar-aprotic solvent is dimethylformamide.

21. The process of claim 2, wherein the range of molar ratio of substituted or unsubstituted aryl triflate to α-stannyl acrylate ester is 1:0.5 to 1:10.

22. The process of claim 21 wherein the molar ratio of substituted or unsubstituted aryl triflate to α-stannyl acrylate ester is 1:2.5.

23. The process of claim 2, wherein the palladium catalyst is bis(triphenylphosphine)palladium(II) chloride, bis(benzonitrile)palladium(II) chloride, trans-benzyl(chloro)bis(triphenylphosphine)palladium(II) or tetrakis(triphenylphosphine)palladium(0).

24. The process of claim 23, wherein the palladium(0) catalyst is terakis(triphenylphosphine)palladium(0).

25. The process of claim 2, wherein the range of molar ratio of terakis(triphenylphosphine)palladium(0) is 1 to 15% of the substituted or unsubstituted aryl triflate.

26. The process of claim 25, wherein the molar ratio of terakis(triphenylphosphine)palladium(0) is 10% of the substituted or unsubstituted aryl triflate.

27. The process of claim 2, wherein the copper(I or II) catalyst is copper(I) iodide, copper(I) bromide, copper(I) cyanide, copper(I) bromide-dimethyl sulfide complex or copper(II) bromide.

28. The process of claim 27, wherein the copper(I or II) catalyst is copper(I) iodide.

29. The process of claim 2, wherein the molar ratio of copper(I) iodide catalyst is 10–150% of the substituted or unsubstituted aryl triflate.

30. The process of claim 29 wherein the the molar ratio of copper(I) iodide is 75% of the substituted or unsubstituted aryl triflate.

31. The process of claim 2, wherein the molar ratio of lithium chloride is 3 times the substituted or unsubstituted aryl triflate.

32. The process of claim 1, wherein α-Methylene-4-nitrobenzeneacetic acid methyl ester is produced.

33. The process of claim 1, wherein α-Methylene-4-(trifluoromethyl)benzeneacetic acid methyl ester is produced.

34. The process of claim 1, wherein 4-Acetyl-α-methylenebenzeneacetic acid methyl ester is produced.

35. The process of claim 1, wherein 4-(Methoxycarbonyl)-α-methylenebenzeneacetic acid methyl ester is produced.

36. The process of claim 1, wherein α-Methylenebenzeneacetic acid methyl ester is produced.

37. The process of claim 1, wherein 4-Methyl-α-methylenebenzeneacetic acid methyl ester is produced.

38. The process of claim 1, wherein 4-Bromo-α-methylenebenzeneacetic acid methyl ester is produced.

39. The process of claim 1, wherein p-Methoxyatropic acid methyl ester is produced.

40. The process of claim 2, wherein 6-Methoxy-α-methylene-2-naphthaleneacetic acid methyl ester is produced.

* * * * *